US011723731B2

(12) United States Patent
Ago et al.

(10) Patent No.: US 11,723,731 B2
(45) Date of Patent: Aug. 15, 2023

(54) ADAPTER SET, ADAPTER, AND METHOD OF MOUNTING SURGICAL INSTRUMENT ON ROBOT ARM THROUGH ADAPTER

(71) Applicant: Medicaroid Corporation, Kobe (JP)

(72) Inventors: Kenji Ago, Kobe (JP); Kazuhiro Sato, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 506 days.

(21) Appl. No.: 17/030,140

(22) Filed: Sep. 23, 2020

(65) Prior Publication Data

US 2021/0093398 A1 Apr. 1, 2021

(30) Foreign Application Priority Data

Sep. 27, 2019 (JP) ................................ 2019-177049

(51) Int. Cl.
*A61B 34/30* (2016.01)
*A61B 46/10* (2016.01)
*A61B 17/00* (2006.01)
*A61B 34/37* (2016.01)

(52) U.S. Cl.
CPC .............. *A61B 34/30* (2016.02); *A61B 46/10* (2016.02); *A61B 34/37* (2016.02); *A61B 2017/00486* (2013.01); *A61B 2017/00973* (2013.01); *A61B 2034/301* (2016.02)

(58) Field of Classification Search
CPC combination set(s) only.
See application file for complete search history.

(56) References Cited

U.S. PATENT DOCUMENTS

| 2007/0119274 A1 | 5/2007 | Devengenzo et al. |
| 2008/0103491 A1 | 5/2008 | Omori et al. |
| 2015/0257841 A1 | 9/2015 | Dachs, II |

(Continued)

FOREIGN PATENT DOCUMENTS

| JP | 2008-104854 A | 5/2008 |
| JP | 2009-520573 A | 5/2009 |

(Continued)

OTHER PUBLICATIONS

Office Action (Notice of Reasons for Refusal) dated Jul. 20, 2021, by the Japanese Patent Office in corresponding Japanese Patent Application No. 2019-177049, and an English translation of the Office Action. (10 pages).

*Primary Examiner* — Scott Luan

(74) *Attorney, Agent, or Firm* — Buchanan Ingersoll & Rooney PC

(57) ABSTRACT

An adapter set is provided with an adapter placed between a robot arm and a surgical instrument, and a stopper mounted on the adapter. The stopper includes a rotation restricting part configured to restrict a rotation of a driving transmission member of the adapter. The driving transmission member includes a first member that includes an engaging depressed part configured to fit together with a driven member of the surgical instrument and another engaging depressed part that is provided separately from the engaging depressed part and is configured to fit together with the rotation restricting part of the stopper, and a second member that includes an engaging depressed part configured to fit together with a driving member. The stopper is configured to be removed from the adapter after the driving member fits together with the second member of the adapter.

20 Claims, 12 Drawing Sheets

(56) References Cited

U.S. PATENT DOCUMENTS

2020/0305991 A1   10/2020  Ago et al.
2020/0305997 A1   10/2020  Ago et al.

FOREIGN PATENT DOCUMENTS

| JP | 5403864 B2 | 11/2013 |
|---|---|---|
| JP | 2017-512557 A | 5/2017 |
| JP | 2020-163101 A | 10/2020 |
| JP | 2020-163104 A | 10/2020 |
| WO | 2007142698 A2 | 12/2007 |
| WO | 2016/176170 A1 | 11/2016 |
| WO | 2018/119136 A1 | 6/2018 |

ADAPTER SET, ADAPTER, AND METHOD OF MOUNTING SURGICAL INSTRUMENT ON ROBOT ARM THROUGH ADAPTER

CROSS-REFERENCE TO RELATED APPLICATION

This application claims priority to Japanese Patent Application No. 2019-177049 filed on Sep. 27, 2019, the entire contents of which are incorporated herein by reference.

BACKGROUND ART

The disclosure relates to an adapter set, an adapter, and a method of mounting a surgical instrument on a robot arm through an adapter.

In the related art, an adapter placed between a robot arm and a surgical instrument is known.

Japanese Patent No. 5403864 discloses an adapter placed between a robot arm and a surgical instrument. Here, in the case of removably mounting a surgical instrument on a robot arm through the adapter, it is necessary for a driving unit of the robot arm and a disk (driving transmission member) of the adapter to reliably fit together. When mounting the adapter on the robot arm, the driving unit is rotationally driven to align the rotational position of the driving unit with the rotational position of the disk of the adapter, and then the driving unit and the disk are fitted together. At this time, friction occurs between the driving unit and disk of the adapter, and in some cases the disk is dragged around by the driving unit. If the disk is dragged around, it is difficult to make the driving unit and the disk engage each other. In Japanese Patent No. 5403864 above, teeth (raised parts) are provided on each of a retractor plate and the disk of the adapter, such that the teeth of the retractor plate and the teeth of the disk are configured to abut each other when the disk is dragged around. With this arrangement, the disk being dragged around is stopped, and the driving unit and the disk are configured to engage each other reliably.

SUMMARY

At this point, to drive a surgical instrument, the disk needs to rotate in association with the rotation of the driving unit of the robot arm. However, with the adapter described in Japanese Patent No. 5403864 above, after the driving unit of the robot arm and the disk engage, an inexpedience may occur in which it is necessary to provide a structure and a space or the like that releases the restriction on the rotation of the disk by the teeth of the retractor plate. For this reason, with the adapter described in Japanese Patent No. 5403864 above, the need for the adapter to have an extra internal structure and internal space creates a problem making it difficult to suppress the dragging around of the disk (driving force transmission member) by the driving unit while also minimizing the complexity and bulkiness of the adapter structure.

This disclosure provides an adapter set and an adapter capable of suppressing the dragging around of the driving transmission member by the driving unit of the robot arm while also minimizing the complexity and bulkiness of the adapter structure.

The adapter set according to a first aspect of the disclosure is provided with: an adapter placed between a driving unit provided in a robot arm and also having a driving member, and a surgical instrument having a driven member; and a stopper mounted on the adapter.

The adapter includes a rotatably provided driving transmission member configured to transmit a driving force from the driving member of the driving unit to the driven member of the surgical instrument. The stopper includes a rotation restricting part configured to restrict a rotation of the driving transmission member. The driving transmission member includes a first member that includes a first engaging part configured to fit together with the driven member of the surgical instrument and a second engaging part that is provided separately from the first engaging part and is configured to fit together with the rotation restricting part of the stopper, and a second member that includes a third engaging part configured to fit together with the driving member of the driving unit. The stopper is configured to be mounted on the adapter in a state in which the rotation of the driving transmission member is restricted by the rotation restricting part before the driving member of the driving unit fits together with the second member of the adapter, and is also configured to be removed from the adapter after the driving member of the driving unit fits together with the second member of the adapter.

An adaptor according to a second aspect of the present disclosure is an adapter placed between a driving unit that is provided in a robot arm and includes a driving member, and a surgical instrument that includes a driven member.

The adapter includes a driving transmission member that is rotatably provided and is configured to transmit a driving force from the driving member of the driving unit to the driven member of the surgical instrument. The driving transmission member includes a first member that includes a first engaging part configured to fit together with the driven member of the surgical instrument and a second engaging part that is provided separately from the first engaging part, and a second member that includes a third engaging part configured to fit together with the driving member of the driving unit, and is mounted in a way so that a stopper that restricts rotation of the driving transmission member fits together with the second engaging part before the driving member of the driving unit fits together with the second member.

A method of mounting a surgical instrument on a robot arm according to a third aspect of the present disclosure is a method of mounting a surgical instrument on a robot arm through an adapter that is placed between the robot arm and the surgical instrument and that includes a driving transmission member configured to transmit a driving force from a driving unit of the robot arm to the surgical instrument.

The method of mounting a surgical instrument on a robot arm includes covering the robot arm with a drape; attaching the adapter to the robot arm covered by the drape, the adapter being in a state in which a stopper configured to restrict a rotation of the driving transmission member is engaged with a second engaging part of the driving transmission member; causing the driving unit of the robot arm and the driving transmission member of the adapter to engage each other; removing the stopper from the adapter after the driving unit of the robot arm and the driving transmission member of the adapter have engaged each other; and attaching the surgical instrument to the adapter with the stopper removed, such that the surgical instrument engages with a first engaging part different from the second engaging part of the driving transmission member.

DETAILED DESCRIPTION

Hereinafter, an embodiment will be described on the basis of the drawings.

(Configuration of Robot Surgical System)

Figure 1:
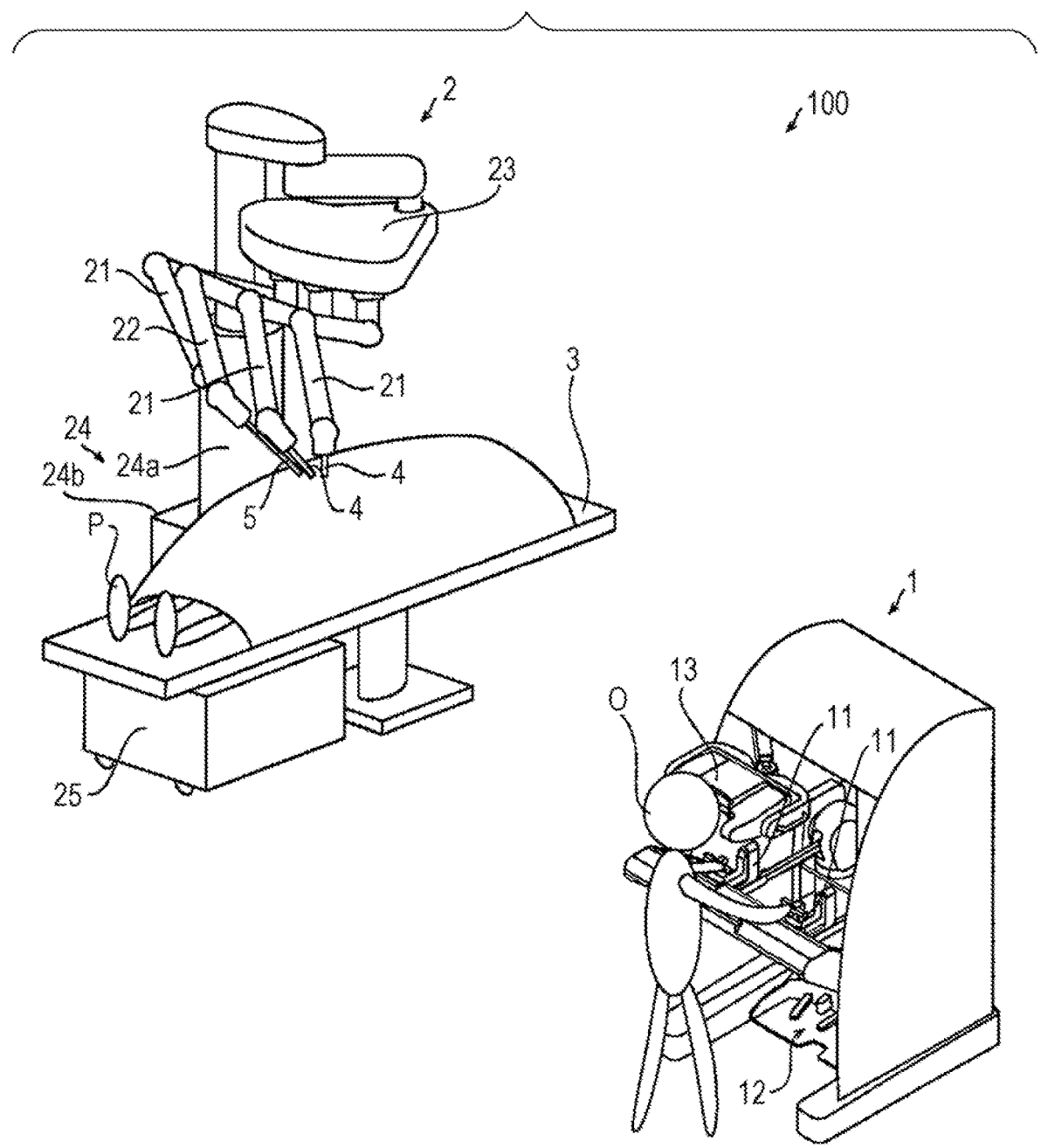
FIG. 1 is a diagram illustrating an overview of a robot surgical system according to an embodiment.
Figure 2:
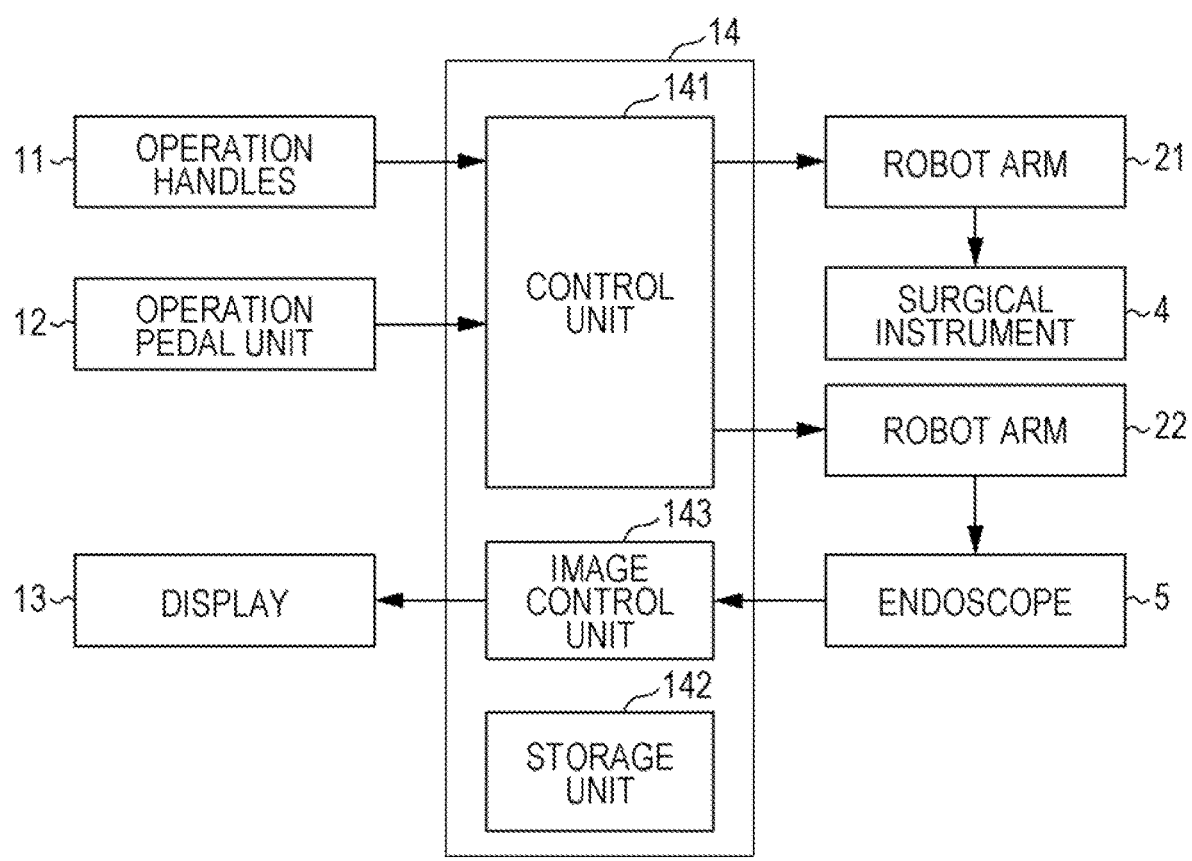
FIG. 2 is a block diagram illustrating a control configuration of the robot surgical system according to the embodiment.

FIGS. 1 and 2 will be referenced to describe the configuration of a robot surgical system 100 according to the embodiment.

As illustrated in FIG. 1, the robot surgical system 100 is provided with a remote operation device 1 and a patient-side device 2. The remote operation device 1 is provided to remotely operate medical equipment provided in the patient-side device 2. When an operating mode command to be executed by the patient-side device 2 is input into the remote operation device 1 by a surgeon acting as an operator O, the remote operation device 1 transmits the operating mode command to the patient-side device 2 through a controller 25. Thereafter, in response to the operating mode command transmitted from the remote operation device 1, the patient-side device 2 operates medical equipment such as a surgical instrument 4 and an endoscope 5 attached to the robot arm 21. With this arrangement, minimally invasive surgery is performed.

The patient-side device 2 forms an interface that performs surgery on a patient P. The patient-side device 2 is disposed beside an operating table 3 on which the patient P lies. The patient-side device 2 includes a plurality of robot arms 21 and 22, and of these, the endoscope 5 is attached to one robot arm 22 while the surgical instrument 4 is attached to another robot arm 21. Each of the robot arms 21 and 22 is commonly supported on a platform 23. The plurality of robot arms 21 and 22 each have a plurality of joints, and each joint is provided with a driving unit including a servo motor and a position detector such as an encoder. The robot arms 21 and 22 are configured to be controlled by a driving signal supplied through the controller 25, such that the medical equipment attached to each of the robot arms 21 and 22 performs a desired movement.

The platform 23 is supported by the positioner 24 placed on the floor of the operating room. In the positioner 24, a pillar 24a having a vertically adjustable lifting axis is coupled to a base 24b provided with wheels and capable of moving across the surface of the floor.

The surgical instrument 4 is removably attached as a piece of medical equipment to the front end of the robot arm 21. The surgical instrument 4 is provided with a housing 41 (see FIG. 3) that is attached to the robot arm 21, a shaft 42 (see FIG. 3) having an elongated shape, and an end effector 43 (see FIG. 3) provided on the front end of the shaft 42. Examples of the end effector 43 include grasping forceps, scissors, a hook, a high-frequency knife, a snare wire, a clamp, and a stapler, but the end effector 43 is not limited to these, and any of various types of treatment tools can be applied. In surgery using the patient-side device 2, the robot arm 21 introduces the surgical instrument 4 into the body of the patient P through an indwelling cannula (trocar) on the body surface of the patient P. Additionally, the end effector 43 of the surgical instrument 4 is placed near a surgical site.

The endoscope 5 is removably attached as a piece of medical equipment to the front end of the robot arm 22. The endoscope 5 takes an image inside the body cavity of the patient P, and the taken image is output to the remote operation device 1. A 3D endoscope capable of taking three-dimensional images or a 2D endoscope is used as the endoscope 5. In surgery using the patient-side device 2, the robot arm 22 introduces the endoscope 5 into the body of the patient P through an indwelling trocar on the body surface of the patient P. Additionally, the endoscope 5 is placed near a surgical site.

The remote operation device 1 forms an interface with the operator O. The remote operation device 1 is a device by which the operator O operates the medical equipment attached to the robot arm 21. In other words, the remote operation device 1 is configured to be capable of transmitting an operating mode command to be executed by the surgical instrument 4 input by the operator O to the patient-side device 2 through the controller 25. The remote operation device 1 is installed near the operating table 3 such that the state of the patient P is easy to see while performing master operations, for example. Note that the remote operation device 1 may also be configured to transmit the operating mode command wirelessly for example, and can also be installed in a separate room from the operating room where the operating table 3 is installed.

An operating mode to be executed by the surgical instrument 4 is a mode of operation achieved by the movement of the surgical instrument 4 (a series of positions and attitudes)

and the function of the surgical instrument 4 individually. For example, in the case where the surgical instrument 4 is grasping forceps, the operating mode to be executed by the surgical instrument 4 refers to a roll rotational position and a pitch rotational position of a wrist of the end effector 43, and an action of opening and closing the jaws. Also, in the case where the surgical instrument 4 is a high-frequency knife, the operating mode to be executed by the surgical instrument 4 may be a vibrational action of the high-frequency knife, specifically the supplying of a current to the high-frequency knife. Also, in the case where the surgical instrument 4 is a snare wire, the operating mode to be executed by the surgical instrument 4 may be an action of tightening the snare and an action of loosening the tightened state of the snare. The operating mode may also be an action of burning off a surgical target site by supplying a bipolar or monopolar current.

The operating mode to be executed by the endoscope 5 refers to setting the position and attitude of the front end of the endoscope 5 or setting the zoom level, for example.

As illustrated in FIGS. 1 and 2, the remote operation device 1 is provided with operation handles 11, an operation pedal unit 12, a display 13, and a control device 14.

The operation handles 11 are provided to remotely operate the medical equipment attached to the robot arm 21. Specifically, the operation handles 11 receive operations performed by the operator O for operating the medical equipment (surgical instrument 4, endoscope 5). Two operation handles 11 are provided in the horizontal direction. In other words, one of the two operation handles 11 is operated by the right hand of the operator O, while the other operation handle 11 is operated by the left hand of the operator O.

Also, the operation handles 11 are disposed to extend forward from the back side of the remote operation device 1. The operation handles 11 are configured to be movable inside a predetermined three-dimensional operation region. In other words, the operation handles 11 are configured to be movable up and down, left and right, and forward and backward.

In the control of the movements of the robot arm 21 and the robot arm 22, the remote operation device 1 and the patient-side device 2 form a master-slave system. In other words, the operation handles 11 form a master operation unit in the master-slave system, while the robot arm 21 and the robot arm 22 to which medical equipment is attached form a slave movement unit. Additionally, when the operator O operates the operation handles 11, the movement of the robot arm 21 or the robot arm 22 is controlled such that the front end of the robot arm 21 (the end effector 43 of the surgical instrument 4) or the front end of the robot arm 22 (the endoscope 5) traces the motion of the operation handles 11.

Also, the patient-side device 2 is configured to control the movement of the robot arm 21 according to a set movement multiplier. For example, in the case where the movement multiplier is set to ½, the end effector 43 of the surgical instrument 4 is controlled to move ½ the distance moved by the operation handles 11. Through this arrangement, delicate surgery can be performed precisely.

The operation pedal unit 12 includes a plurality of pedals for executing functions related to the medical equipment. The plurality of pedals include a coagulation pedal, a cutting pedal, a camera pedal, and a clutch pedal. Also, the plurality of pedals are operated by the feet of the operator O.

The coagulation pedal is capable of using the surgical instrument 4 to perform an operation causing the surgical site to coagulate. Specifically, by operating the coagulation pedal, a voltage for coagulation is applied to the surgical instrument 4, and coagulation of the surgical site is performed. The cutting pedal is capable of using the surgical instrument 4 to perform an operation of cutting the surgical site. Specifically, by operating the cutting pedal, a voltage for cutting is applied to the surgical instrument 4, and cutting of the surgical site is performed.

The camera pedal is used to manipulate the position and attitude of the endoscope 5 that images the interior of the body cavity. Specifically, the camera pedal enables the endoscope 5 to be operated with the operation handles 11. In other words, while the camera pedal is pressed, the position and attitude of the endoscope 5 can be manipulated with the operation handles 11. For example, the endoscope 5 is operated by using both of the left and right operation handles 11. Specifically, by causing the left and right operation handles 11 to revolve about the midpoint between the left and right operation handles 11, the endoscope 5 is made to turn. Also, by pushing in both the left and right operation handles 11 together, the endoscope 5 advances forward. Also, by pulling both the left and right operation handles 11 together, the endoscope 5 pulls back. Also, by moving both the left and right operation handles 11 up, down, left, or right together, the endoscope 5 moves up, down, left, or right.

The clutch pedal is used in the case of temporarily interrupting the operation connected between the robot arm 21 and the operation handles 11 to stop the action of the surgical instrument 4. Specifically, while the clutch pedal is being operated, the robot arm 21 of the patient-side device 2 does not move even if the operation handles 11 are operated. For example, in the case where an operation has caused the operation handles 11 to come near the edge of the movable range, operating the clutch pedal makes it possible to temporarily interrupt the operation connection and return the operation handles 11 to a position near the center. Thereafter, if the operation of the clutch pedal is stopped, the robot arm 21 and the operation handles 11 are reconnected and the operation of the operation handles 11 can be resumed near the center.

The display 13 is capable of displaying the image taken by the endoscope 5. The display 13 includes a scope display or a non-scope display. A scope display refers to a display that the operator peers into, for example. Also, a non-scope display includes an open display having a flat screen that the operator does not peer into, like the display of an ordinary personal computer.

In the case where a scope display is attached, a 3D image taken by the endoscope 5 attached to the robot arm 22 of the patient-side device 2 is displayed. A 3D image taken by the endoscope 5 provided on the patient-side device 2 is also displayed in the case where a non-scope display is attached. Note that in the case where a non-scope display is attached, a 2D image taken by the endoscope 5 provided on the patient-side device 2 may also be displayed.

As illustrated in FIG. 2, the control device 14 includes a control unit 141 having an arithmetic unit such as a CPU, a storage unit 142 having memory such as ROM and RAM, and an image control unit 143. The control device 14 may be configured as a single control device that provides centralized control, or as a plurality of control devices that cooperate with each other to provide decentralized control. The control unit 141 determines whether the operating mode command input by the operation handles 11 is an operating mode command to be executed by the robot arm 21 or an operating mode command to be executed by the endoscope 5, according to the toggle state of the operation pedal unit 12. Additionally, if the operating mode command input by the operation handles 11 is determined to be an operating mode command to be executed by the surgical instrument 4, the control unit 141 transmits the operating mode command to the robot arm 21. With this arrangement, the robot arm 21 is driven, and the movement of the surgical instrument 4 attached to the robot arm 21 is controlled by the driving.

Also, if the operating mode command input by the operation handles 11 is determined to be an operating mode command to be executed by the endoscope 5, the control unit 141 transmits the operating mode command to the robot arm 22. With this arrangement, the robot arm 22 is driven, and the movement of the endoscope 5 attached to the robot arm 22 is controlled by the driving.

Control programs corresponding to types of surgical instruments 4 for example are stored in the storage unit 142, and by having the control unit 141 read out these control programs according to the type of attached surgical instrument 4, the operation handles 11 of the remote operation device 1 and/or the operating commands of the operation pedal unit 12 can be made to operate in accordance with individual surgical instruments 4.

The image control unit 143 transmits the image acquired by the endoscope 5 to the display 13. The image control unit 143 processes and corrects the image as necessary.
(Configuration of Adapter and Surgical Instrument)

FIGS. 3 to 18 will be referenced to describe the configuration of an adapter 6a and the surgical instrument 4 according to the embodiment.

Figure 3:
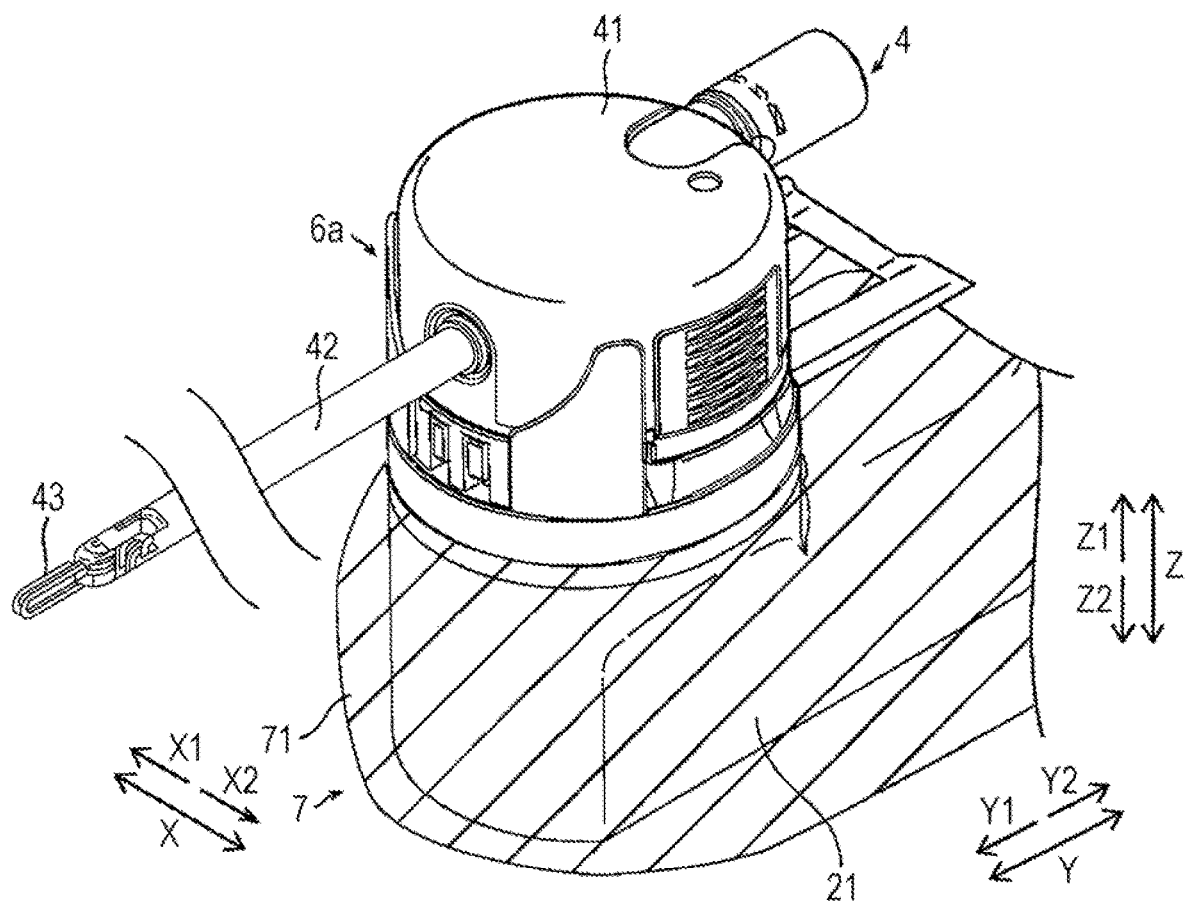
FIG. 3 is a perspective view illustrating a state in which a surgical instrument is attached to a robot arm through an adapter according to the embodiment.
Figure 4:
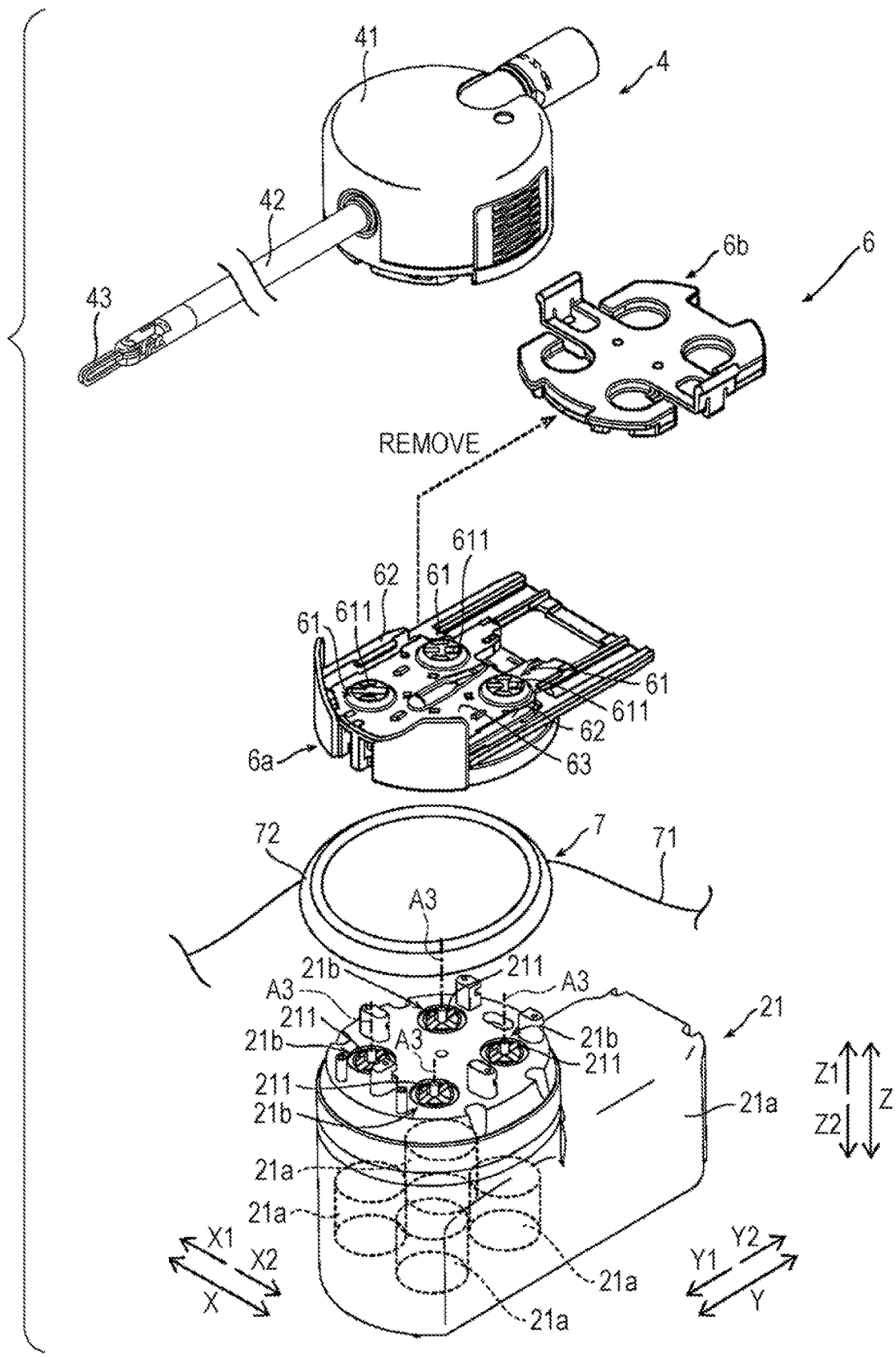
FIG. 4 is a perspective view illustrating a state before the adapter and the surgical instrument are attached to the robot arm according to the embodiment.

As illustrated in FIGS. 3 and 4, the surgical instrument 4 is removably connected to the robot arm 21 through an adapter 6a. The adapter 6a is a drape adapter for inserting a sterilized drape 7 for covering the robot arm 21 between itself and the robot arm 21. In other words, the adapter 6a is configured such that the drape 7 is attachable. With this arrangement, when the adapter 6a is attached to the robot arm 21, by attaching the drape 7 between the robot arm 21 and the adapter 6a, a sterile zone and a contaminated zone can be isolated reliably. Also, the adapter 6a is placed between driving units 21a provided in the robot arm 21 and including driving members 21b, and the surgical instrument 4 including a driven member 44.

The surgical instrument 4 is attached on the Z1 direction side of the adapter 6a. The adapter 6a is attached on the Z1 direction side of the robot arm 21.

The robot arm 21 is used in the sterile zone, and therefore is covered by the drape 7. At this point, in the operating room, a sterilization operation is performed to prevent the area cut open by surgery as well as medical equipment from being contaminated by pathogens, foreign matter, and the like. In the sterilization operation, a sterile zone and a contaminated zone are set, the contaminated zone being the zone outside the sterile zone. The surgical site is positioned in the sterile zone. During surgery, members of a surgical team including the operator O take care to position only disinfected objects in the sterile zone, and in addition, when moving an object positioned in the contaminated zone to the sterile zone, a sterilization process is performed on the object. Similarly, when a member of the surgical team including the operator O positions his or her hands in the contaminated zone, the member sterilizes his or her hands before directly touching an object positioned in the sterile zone. Equipment used in the sterile zone is subjected to the sterilization process or covered by the sterilized drape 7.

As illustrated in FIG. 4, the drape 7 is provided with a main body 71 and an attaching part 72. The main body 71 is formed in a film. The attaching part 72 is formed by resin molding. The attaching part 72 is provided with a through-hole in a portion that engages with the robot arm 21 and the adapter 6a. A through-hole may also be provided in correspondence with each engaging portion. In addition, a through-hole may also be provided in correspondence with a plurality of engaging portions.

Figure 5:
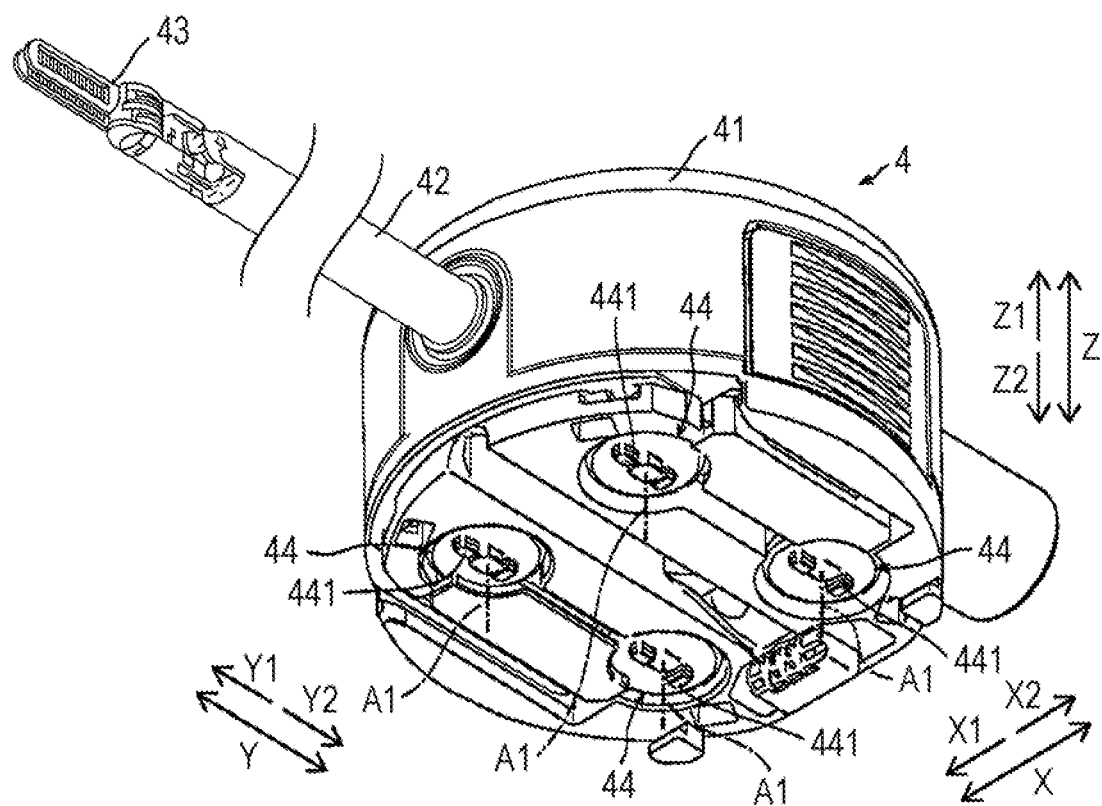
FIG. 5 is a perspective view from below of the surgical instrument according to the embodiment.

As illustrated in FIG. 5, the surgical instrument 4 has a plurality of (four) driven members 44. The driven members 44 are provided inside the housing 41 so as to be rotatable about a rotation axis line A1 extending in the Z direction. The plurality of driven members 44 are provided to operate (drive) the end effector 43. For example, the driven members 44 are connected to the end effector 43 by wires or cables (not illustrated) inserted into the shaft 42. With this arrangement, the wires or cables are driven according to the rotation of the driven members 44, while in addition, the end effector 43 is operated (driven) according to the driving of the wires or cables. As another example, the driven members 44 are connected to the shaft 42 through gears (not illustrated). With this arrangement, the shaft 42 is rotated according to the rotation of the driven members 44, while in addition, the end effector 43 is operated according to the rotation of the shaft 42.

Each of the plurality of driven members 44 includes an engaging raised part 441 that engages with a driving transmission member 61 described later of the adapter 6a, such that driving force from the robot arm 21 is transmitted to the end effector 43. The engaging raised parts 441 project outward from the surface on the Z2 direction side of the driven members 44 toward the adapter 6a (Z2 direction side). Also, the engaging raised parts 441 have shapes that correspond to engaging depressed parts 611 (see FIG. 4) described later of the adapter 6a. Note that the engaging depressed parts 611 are an example of a first engaging part.

Figure 6:
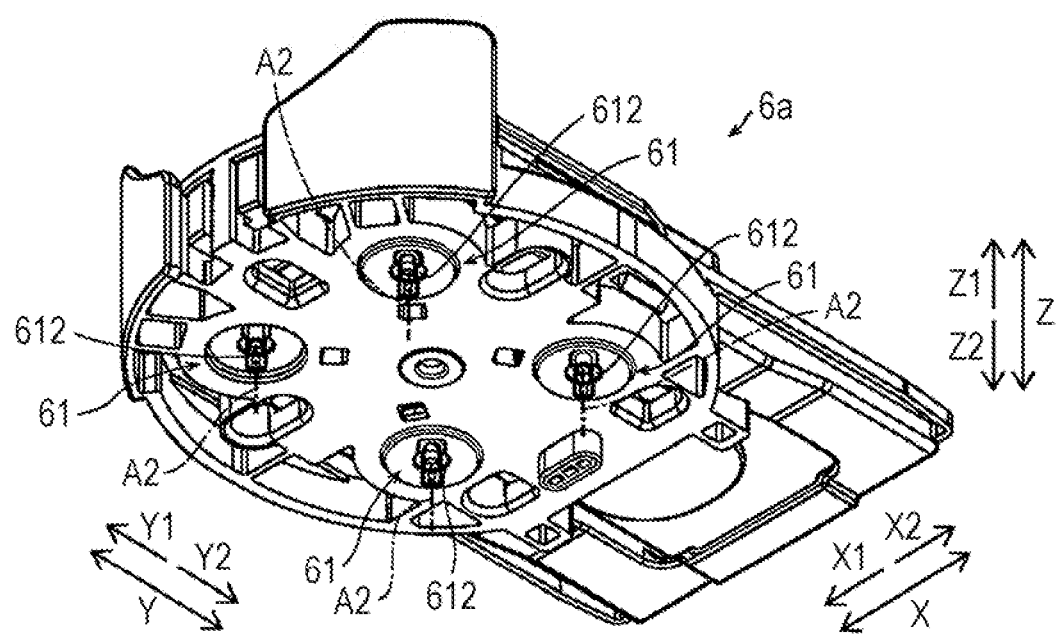
FIG. 6 is a perspective view from below of the adapter according to the embodiment.

As illustrated in FIGS. 4 and 6, the adapter 6a includes a plurality of (four) driving transmission members 61 and a pair of guide rails 62. The driving transmission members 61 are configured to transmit driving force from the driving members 21b of the driving units 21a of the robot arm 21 to the driven members 44 of the surgical instrument 4. In other words, the driving transmission members 61 are provided in correspondence with the driven members 44 of the surgical instrument 4. The driving transmission members 61 are provided so as to be rotatable about a rotation axis line A2 extending in the Z direction.

As illustrated in FIG. 4, each of the plurality of driving transmission members 61 includes the engaging depressed part 611 that engages with the engaging raised part 441 (see FIG. 5) of each driven member 44 of the surgical instrument 4. The engaging depressed part 611 is provided on the surgical instrument 4 side (Z1 direction side) of the driving transmission member 61, and in addition, is depressed from the surface on the Z1 direction side of the driving transmission member 61 toward the opposite side (Z2 direction side) of the surgical instrument 4.

As illustrated in FIG. 6, each of the plurality of driving transmission members 61 includes an engaging depressed part 612 that engages with an engaging raised part 211 (see FIG. 4) described later of the robot arm 21. The engaging depressed parts 612 are provided on the robot arm 21 side (Z2 direction side) of each driving transmission member 61. The engaging depressed parts 612 are depressed from the surface on the Z2 direction side of the driving transmission member 61 toward the opposite side (Z1 direction side) of the robot arm 21. Note that the plurality of driving transmission members 61 have substantially the same configuration as each other. Note that the engaging depressed parts 612 are an example of a third engaging part.

Figure 7:
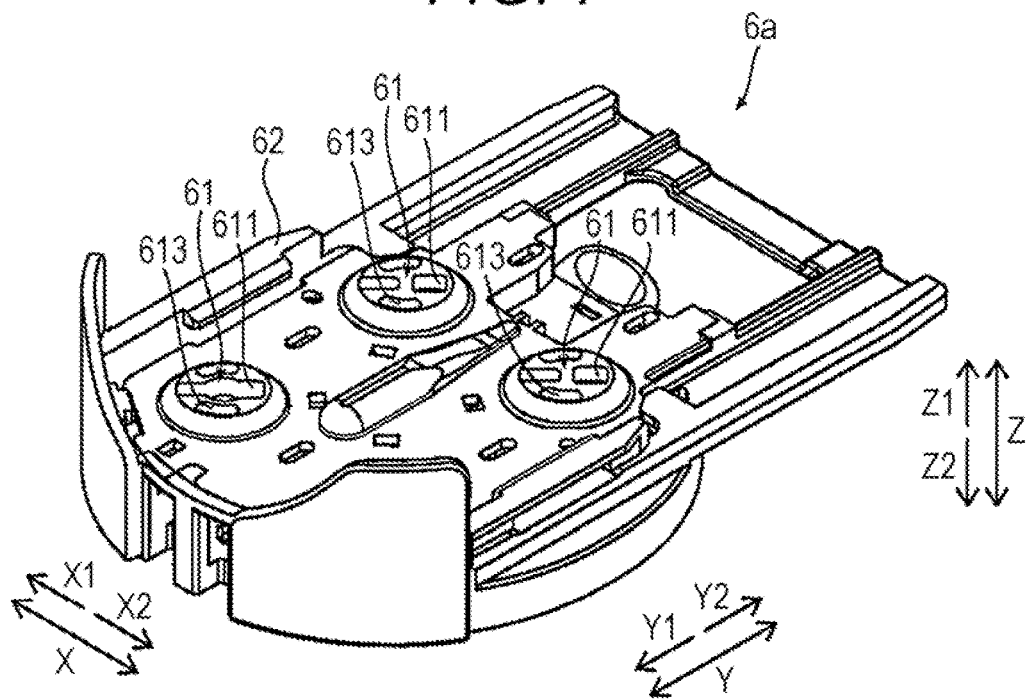
FIG. 7 is a perspective view from above of the adapter according to the embodiment.
Figure 8:
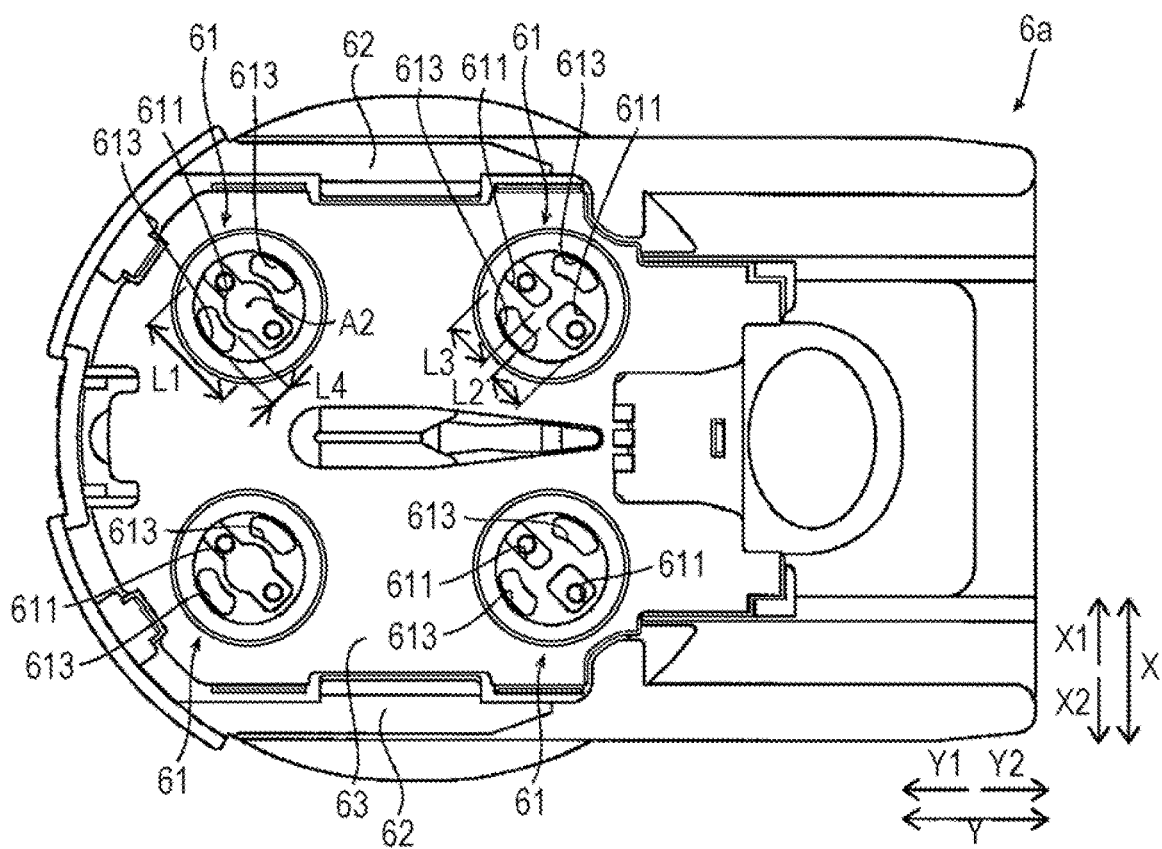
FIG. 8 is a plan view from above of the adapter according to the embodiment.

As illustrated in FIGS. 7 and 8, the pair of guide rails 62 are configured to guide a sliding movement of the surgical instrument 4 in the Y1 direction when attaching the surgical instrument 4 to the adapter 6a. Specifically, the pair of guide rails 62 are provided on a surface 63 on the Z1 direction side of the adapter 6a. The pair of guide rails 62 are provided extending in the Y direction. The pair of guide rails 62 face each other in the X direction.

Here, in the present embodiment, as illustrated in FIGS. 7 and 8, engaging depressed parts 613 that fit together with rotation restricting parts 65 (see FIG. 11) of a stopper 6b are provided separately from the engaging depressed parts 611. With this arrangement, even in the case where the engaging depressed parts 611 are shaped into a special shape for suppressing a loss of the fit between the driven members 44 of the surgical instrument 4 and the engaging depressed parts 611 of the adapter 6a, unlike the case where the stopper 6b and the engaging depressed parts 611 are made to engage, it is not necessary to shape the stopper 6b into a special shape to match the shape of the engaging depressed parts 611. With this arrangement, an increase in the complexity of the structure of the stopper 6b can be avoided. Note that the engaging depressed parts 613 are an example of a second engaging part.

Also, the engaging depressed parts 611 and the engaging depressed parts 613 are formed as depressed shapes in the driving transmission members 61. Also, the rotation restricting parts 65 of the stopper 6b are formed as raised shapes. With this arrangement, because the engaging depressed parts 611 and the engaging depressed parts 613 are both formed as depressed shapes, when the surgical instrument 4 is slid to be attached to the adapter 6a, unlike the case where either the engaging depressed parts 611 or the engaging depressed parts 613 are formed as raised shapes, a situation where the surgical instrument 4 is caught on the raised portions can be avoided.

Also, the engaging depressed parts 611 and the engaging depressed parts 613 have different shapes from each other as seen in the rotation axis line A2 direction of the driving transmission members 61. With this arrangement, a situation in which the driven members 44 of the surgical instrument 4 that fit together with the engaging depressed parts 611 are incorrectly fitted together with the engaging depressed parts 613 can be avoided. Specifically, the engaging depressed parts 611 are substantially rectangular as seen from the rotation axis direction (as seen from the Z1 direction side), while the engaging depressed parts 613 are substantially arc-shaped curving along the rim of the driving transmission members 61 as seen from the rotation axis direction (as seen from the Z1 direction side). The engaging depressed parts 611 and the engaging depressed parts 613 have different lengths in the radial direction of the driving transmission members 61. With this arrangement, a situation in which the driven members 44 of the surgical instrument 4 that fit together with the engaging depressed parts 611 are incorrectly fitted together with the engaging depressed parts 613 can be avoided, regardless of the rotational position of the driving transmission members 61.

The engaging depressed parts 611 of the driving transmission members 61 disposed on the Y1 direction side have a length of L1 in the radial direction. Also, each driving transmission member 61 disposed on the Y2 direction side is provided with two engaging depressed parts 611. The two engaging depressed parts 611 have lengths of L2 and L3 in the radial direction, respectively. On the other hand, the engaging depressed parts 613 provided in the driving transmission members 61 have a length of L4 in the radial direction. L1, L2, L3, and L4 are mutually different lengths. Also, the length L4 in the radial direction of the engaging depressed parts 613 is smaller than the lengths L1, L2, and L3 in the radial direction of the engaging depressed parts 611. Consequently, the driven members 44 of the surgical instrument 4 do not enter the engaging depressed parts 613 at any rotational position of the driving transmission members 61.

Figure 12:
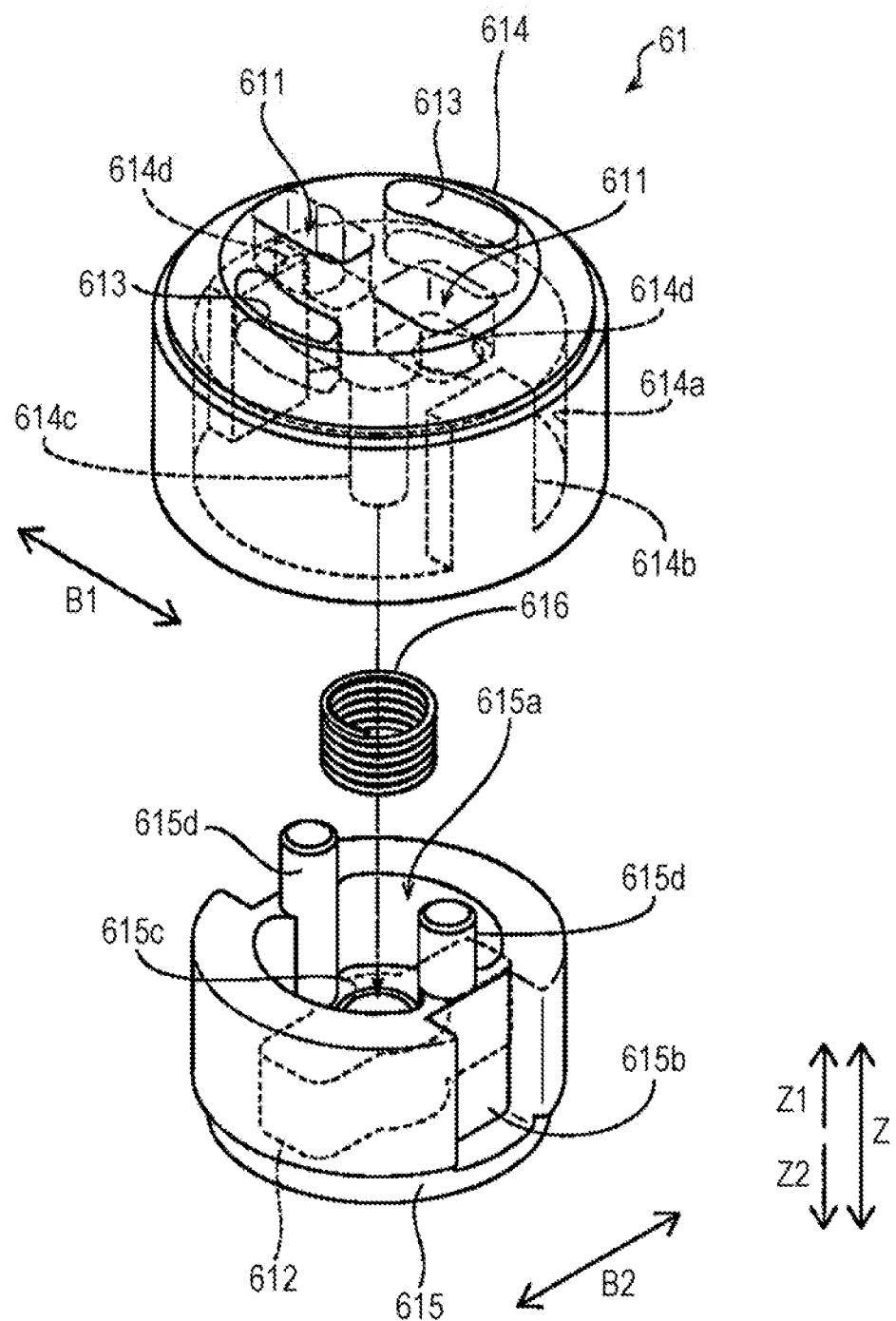
FIG. 12 is an exploded perspective view of a driving transmission member of the adapter according to the embodiment.

Also, as illustrated in FIG. 12, each driving transmission member 61 includes a first member 614 disposed on the Z1 direction side and a second member 615 disposed on the Z2 direction side. The engaging depressed parts 613 are plurally provided in the first member 614. Also, as illustrated in FIG. 8, the plurality of engaging depressed parts 613 are disposed rotationally asymmetrically as seen in the rotation axis line A2 direction. With this arrangement, because the plurality of engaging depressed parts 613 can be fitted together with the rotation restricting parts 65 of the stopper 6b only at a specific rotational position of the driving transmission members 61, the adapter 6a can be attached to the robot arm 21 in a state where the driving transmission members 61 are positioned in the specific rotational position.

Specifically, a pair of the engaging depressed parts 613 is provided in the first member 614. Also, the pair of engaging depressed parts 613 is disposed point-asymmetrically with respect to the center of rotation of each driving transmission member 61. With this arrangement, by fitting the pair of engaging depressed parts 613 disposed point-asymmetrically together with the rotation restricting parts 65 of the stopper 6b, the driving transmission members 61 can be positioned in the specific rotational position easily. Also, the pair of engaging depressed parts 613 are disposed line-symmetrically with respect to a straight line passing through the center of rotation of each driving transmission member 61 (a straight line in the extension direction of the engaging depressed parts 611). With this arrangement, by fitting the pair of engaging depressed parts 613 disposed line-symmetrically together with the rotation restricting parts 65 of the stopper 6b, the rotation of the driving transmission members 61 can be restricted in a balanced way.

As illustrated in FIG. 4, the robot arm 21 includes the driving units 21a provided with the driving members 21b. A plurality of (four) driving units 21a and driving members 21b are provided. The plurality of driving members 21b are provided in correspondence with the plurality of (four) driving transmission members 61 of the adapter 6a. Each of the driving units 21a includes a motor and an encoder. The driving units 21a are configured to rotationally drive the driving members 21b. Each of the driving members 21b includes the engaging raised part 211. The engaging raised parts 211 are configured to fit together with the engaging depressed parts 612 of the driving transmission members 61. The driving members 21b are provided so as to be rotatable about a rotation axis line A3 extending in the Z direction.

(Configuration of Stopper)

As illustrated in FIG. 4, the stopper 6b is configured to be removably attached to the adapter 6a. An adapter set 6 is provided with the adapter 6a and the stopper 6b.

Figure 9:
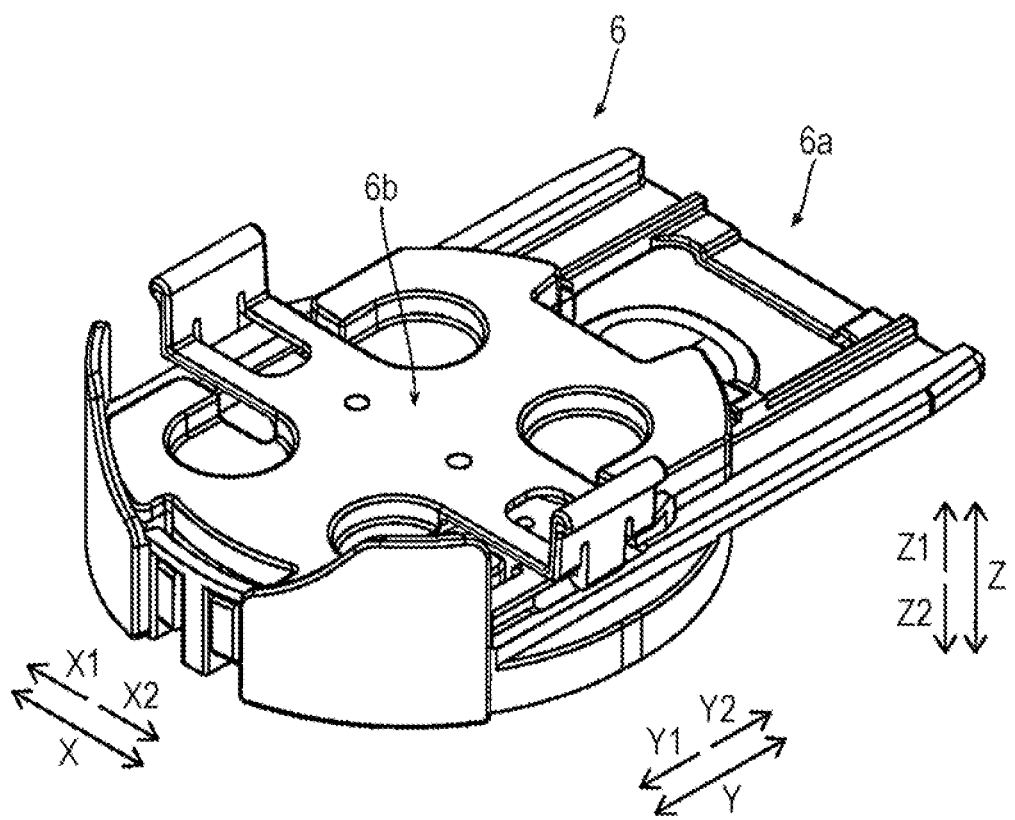
FIG. 9 is a perspective view illustrating a state in which a stopper is attached to the adapter according to the embodiment.

As illustrated in FIG. 9, the stopper 6b is attached to the adapter 6a in a state where the rotational position of the driving transmission members 61 of the adapter 6a is locked in position. Here, locked in position means that the rotational angle of the driving transmission members 61 of the adapter 6a is held at a predetermined position.

Figure 10:
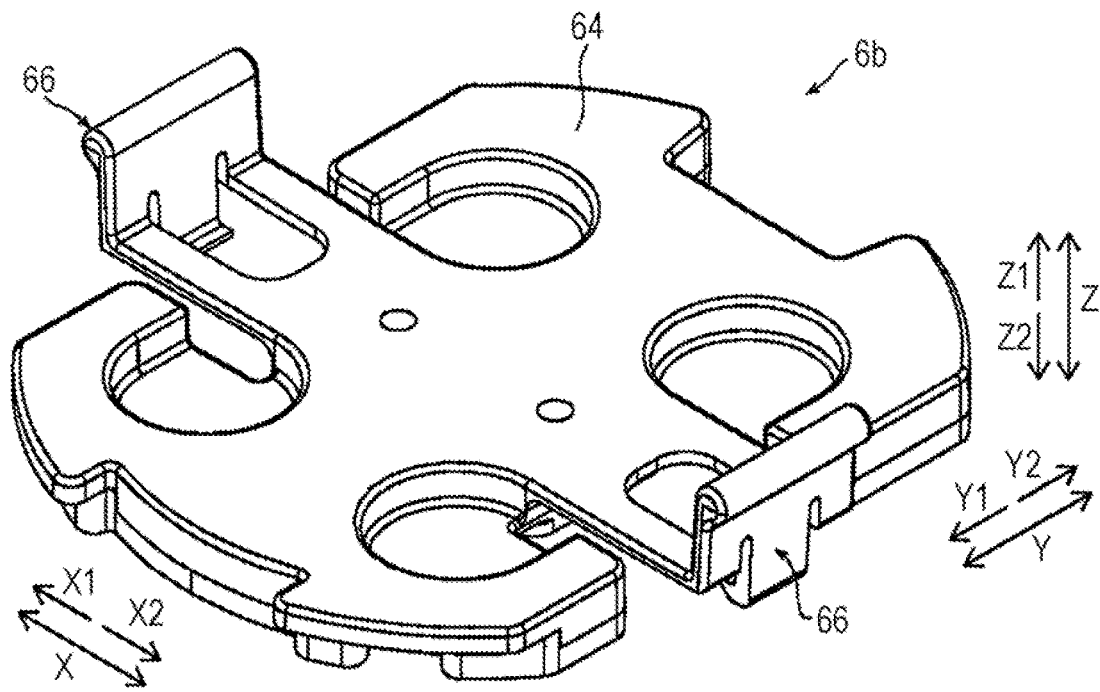
FIG. 10 is a perspective view from above of the stopper according to the embodiment.
Figure 11:
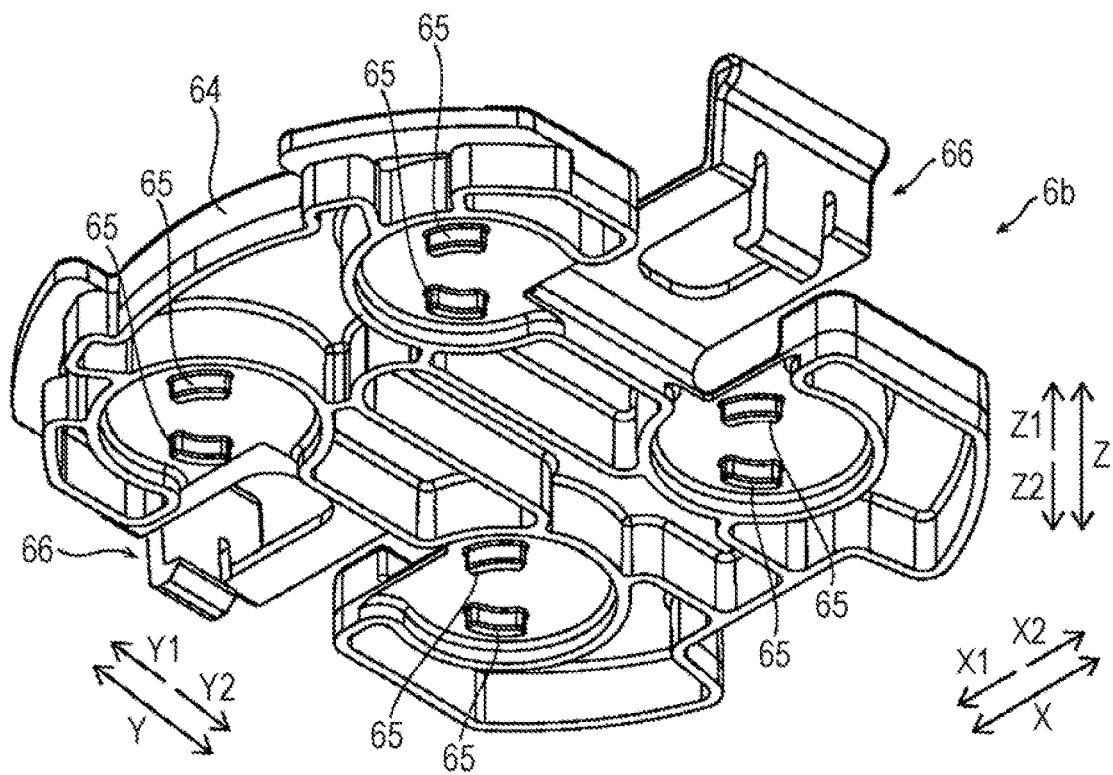
FIG. 11 is a perspective view from below of the stopper according to the embodiment.

Specifically, as illustrated in FIGS. 10 and 11, the stopper 6b includes a stopper body 64 and rotation restricting parts 65 that are provided in the stopper body 64 and that restrict the rotation of the driving transmission members 61 (see FIGS. 7 and 8). The stopper 6b is configured to be mounted on the adapter 6a in a state where the rotation of the driving transmission members 61 is restricted by the rotation restricting parts 65 before the driving members 21b of the driving units 21a fit together with the second member 615 of the adapter 6a. Also, the stopper 6b is configured to be removed from the adapter 6a after the driving members 21b of the driving units 21a fit together with the second member 615 of the adapter 6a. With this arrangement, because the stopper 6b is removed when the surgical instrument 4 is mounted onto the driving units 21a through the adapter 6a, it is not necessary to provide a structure for restricting the rotation of the driving transmission members 61 in the adapter 6a itself. As a result, because the rotation of the driving transmission members 61 is restricted by the rotation restricting parts 65 of the stopper 6b without provided an extra internal structure and internal space in the adapter 6a, it is possible to suppress the dragging around of the driving transmission members 61 by the driving units 21a of the robot arm 21 while also minimizing the complexity and bulkiness of the structure of the adapter 6a.

The stopper body 64 is formed with a resin material such as polypropylene. The stopper body 64 is formed to have thin walls. As seen from the Z1 direction side, the stopper body 64 has a shape corresponding to the surface 63 on the Z1 direction side of the adapter 6a (see FIG. 4). The surface on the Z1 direction side of the stopper body 64 is formed to be substantially flat. The surface on the Z2 direction side of the stopper body 64 has a plurality of raised and depressed areas to reduce the wall thickness.

The stopper body 64 includes attaching parts 66 that removably attach the stopper body 64 to the adapter 6a (see FIG. 4). The attaching parts 66 are configured to attach the stopper body 64 in a locked position with respect to the adapter 6a, and also to remove the stopper body 64 in an unlocked position with respect to the adapter 6a.

The stopper 6b is attached to the adapter 6a with the pair of attaching parts 66 gripping the pair of guide rails 62 on the adapter 6a in the X direction.

The rotation restricting parts 65 are configured to fit together with the engaging depressed parts 613 of the adapter 6a. Also, two rotation restricting parts 65 are provided for each driving transmission member 61. Also, the rotation restricting parts 65 have a raised shape corresponding to the shape of the engaging depressed parts 613. In other words, the pair of rotation restricting parts 65 is disposed point-asymmetrically with respect to the center of rotation of each driving transmission member 61. Also, the pair of rotation restricting parts 65 is disposed line-asymmetrically with respect to a straight line passing through the center of rotation of each driving transmission member 61.

As illustrated in FIG. 12, each driving transmission member 61 includes the first member 614 and the second member 615. The first member 614 includes the engaging depressed parts 611 that fit together with the driven members 44 of the surgical instrument 4, and the engaging depressed parts 613 that are provided separately from the engaging depressed parts 611 and that fit together with the rotation restricting parts 65 of the stopper 6b. The second member 615 includes the engaging depressed part 612 that fits together with the corresponding driving member 21b of the corresponding driving unit 21a of the robot arm 21. Also, each driving transmission member 61 includes a spring 616.

The first member 614 is disposed on the side where the surgical instrument 4 is attached (Z1 direction side). The second member 615 is disposed on the side attached to the robot arm 21 (Z2 direction side). In addition, the second member 615 includes a housing depressed part 615a that houses the spring 616. The first member 614 and the second member 615 fit together to be movable relative to each other in the Z direction with the spring 616 positioned in between. Also, the first member 614 and the second member 615 are held by the adapter 6a to be movable relative to each other in the Z direction. Although FIG. 12 illustrates the driving transmission members 61 provided on the Y2 direction side, the same applies to the driving transmission members 61 provided on the Y1 direction side.

The first member 614 is provided to be movable in the Z direction relative to the second member 615 through the spring 616. In other words, the first member 614 is provided to be movable toward the surgical instrument 4 (Z1 direction) and toward the corresponding driving unit 21a (Z2 direction) relative to the second member 615 through the spring 616. With this arrangement, the spring 616 can be used to cause the first member 614 to move easily relative to the second member 615. Also, when mounting the surgical instrument 4 on the adapter 6a, the first member 614 of each driving transmission member 61 can be moved to be depressed in the Z2 direction. Additionally, the second member 615 is provided to be movable in the Z direction relative to the first member 614 through the spring 616. In other words, the second member 615 is provided to be movable toward the surgical instrument 4 (Z1 direction) and toward the corresponding driving unit 21a (Z2 direction) relative to the first member 614 through the spring 616. With this arrangement, the spring 616 can be used to cause the second member 615 to move easily relative to the first member 614. Also, when mounting the adapter 6a to the driving units 21a of the robot arm 21, the second member 615 of each driving transmission member 61 can be moved to be depressed in the Z1 direction. The spring 616 biases the first member 614 in the Z1 direction and biases the second member 615 in the Z2 direction. The spring 616 is a compression spring (compression coil spring).

Also, the first member 614 and the second member 615 are configured to rotate as one about the rotation axis line A2 extending in the Z direction. Specifically, the first member 614 has fitting raised parts 614b that fit together with the second member 615 to engage the second member 615 in the rotational direction. Also, the second member 615 has fitting depressed parts 615b that fit together with the first member 614 to engage the first member 614 in the rotational direction. The fitting raised parts 614b are provided to project inwardly from the inner perimeter of a fitting depressed part 623a of the first member 614, and engage the fitting depressed parts 615b of the second member 615. The fitting depressed parts 615b are provided to be depressed inwardly from the outer perimeter of the second member 615, and engage the fitting raised parts 614b of the first member 614. Additionally, the fitting depressed parts 615b of the second member 615 and the fitting raised parts 614b of the first member 614 are provided to maintain the engaged state with each other even in the case where the first member 614 or the second member 615 moves in the Z direction through the spring 616. With this arrangement, each driving transmission member 61 is configured such that the first member 614 and the second member 615 rotate as one even in the case where the first member 614 or the second member 615 moves in the Z direction through the spring 616.

Also, the second member 615 has a through-hole 615c provided inside the engaging depressed part 612. The through-hole 615c penetrates through the second member 615 in the rotation axis direction (Z direction) in which the rotation axis line A2 extends. The through-hole 615c is substantially circular as seen from the rotation axis direction. The first member 614 has an inserted part 614c that is inserted in the Z direction into the through-hole 615c of the second member 615. The inserted part 614c is provided to extend in the rotational axis direction. The inserted part 614c has a substantially columnar shape. The through-hole 615c of the second member 615 and the inserted part 614c of the first member 614 are both provided at the center of rotation of each driving transmission member 61. Also, the spring 616 is provided to surround the inserted part 614c.

The second member 615 has projections 615d that act as movement restricting parts that restrict the movement of the second member 615 toward the surgical instrument 4 (Z1 direction) by abutting the corresponding driven member 44 of the surgical instrument 4 in the case where the corresponding driving member 21b of the corresponding driving unit 21a is fitted together with the engaging depressed part 612 of the second member 615 and the corresponding driven member 44 of the surgical instrument 4 is fitted together with the engaging depressed part 611 of the first member 614. With this arrangement, because the movement of the second member 615 toward the surgical instrument 4 can be suppressed, a loss of the fit between the corresponding driving member 21b of the corresponding driving unit 21a and the engaging depressed part 612 of the second member 615 can be suppressed effectively.

Through-holes 614d are provided in the engaging depressed parts 611 of the first member 614. The projections 615d that act as movement restricting parts are formed to extend in the rotation axis line A2 direction of each driving transmission member 61. Also, the projections 615d are inserted into the through-holes 614d of the engaging depressed parts 611. With this arrangement, even in the case where the projections 615d that act as movement restricting parts are positioned in the engaging depressed parts 611, unlike the case where the rotation restricting parts 65 of the stopper 6b are made to engage with the engaging depressed parts 611, a loss of the fit with the rotation restricting parts 65 of the stopper 6b by the projections 615d that act as movement restricting parts can be suppressed.

The engaging depressed parts 611 of the first member 614 are provided extending in a first direction B1 in the radial direction of each driving transmission member 61. Also, the engaging depressed part 612 of the second member 615 is provided extending in a second direction B2 substantially orthogonal to the first direction B1 in the radial direction of each driving transmission member 61. With this arrangement, by providing the engaging depressed parts 611 of the first member 614 with a fitting gap in the first direction B1 and providing the engaging depressed part 612 of the second member 615 with a fitting gap in the second direction B2, the directions of the fitting gaps of the engaging depressed parts 611 and the engaging depressed part 612 can be made to be substantially orthogonal to each other, thereby making it possible to suppress an increase in rattling and wobbling caused by the fitting gaps.

(Attaching Surgical Instrument to Robot Arm)

FIGS. 13 to 16 will be referenced to describe how the surgical instrument 4 is attached to the robot arm 21 according to the embodiment.

Figure 13:
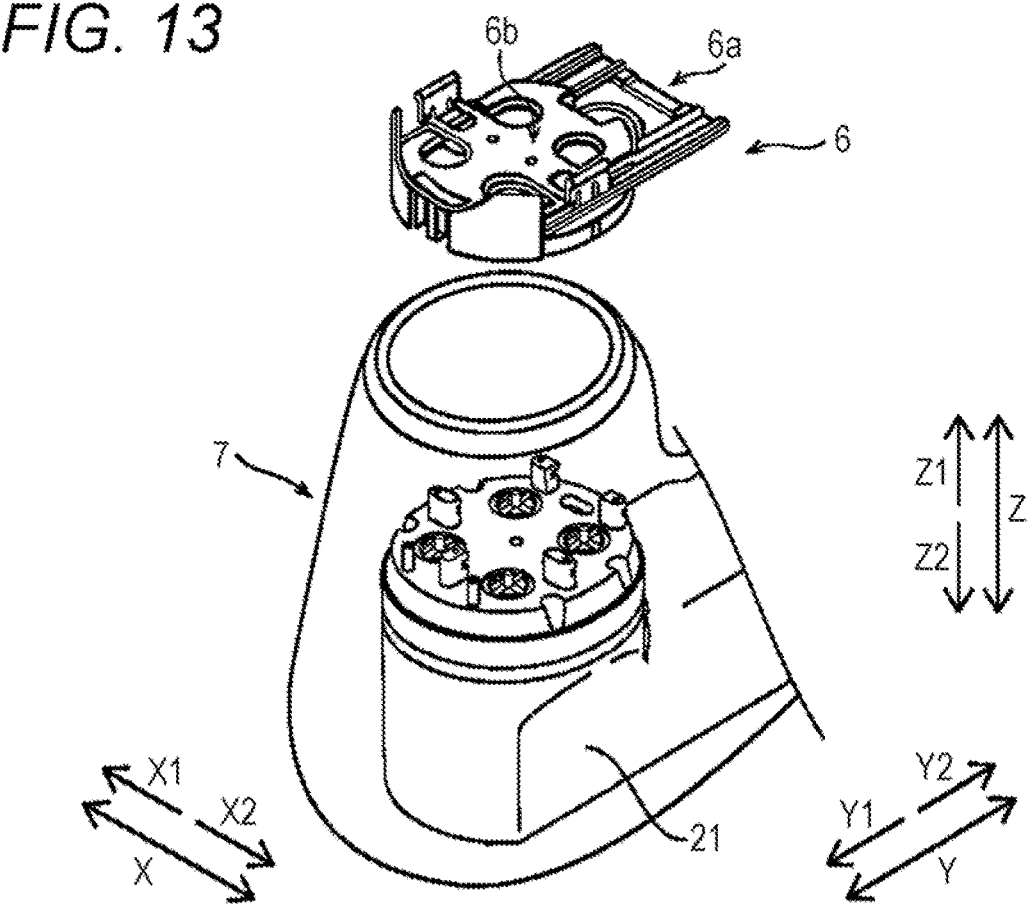
FIG. 13 is a diagram for explaining the attachment of the adapter to the robot arm according to the embodiment.
Figure 14:
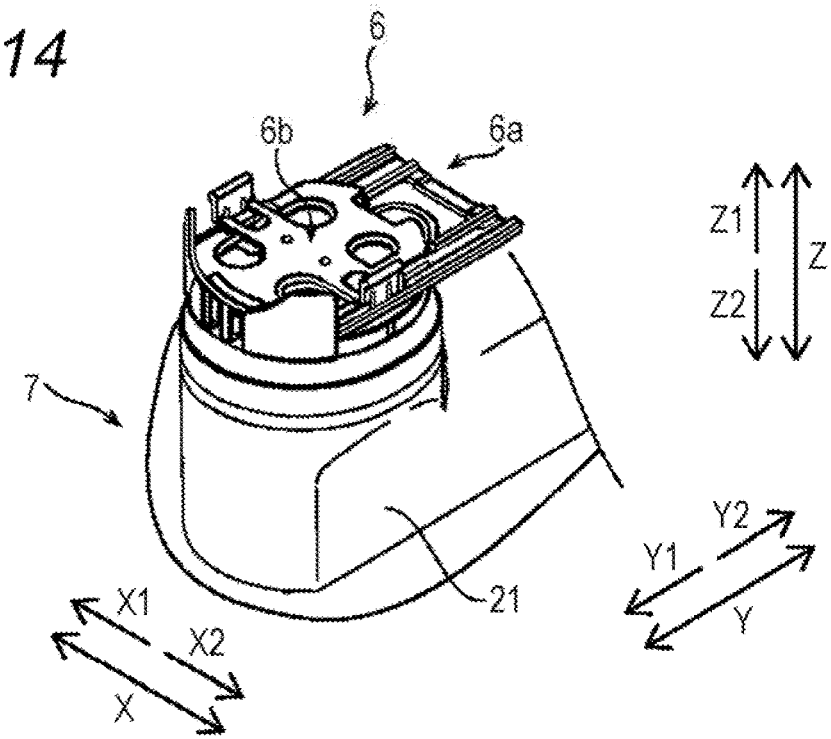
FIG. 14 is a diagram illustrating a state in which the adapter is attached to the robot arm according to the embodiment.

As illustrated in FIGS. 13 and 14, with the robot arm 21 covered by the drape 7, the adapter 6a with the stopper 6b mounted thereon is attached to the robot arm 21. The adapter 6a is attached to the robot arm 21 by being moved in the Z direction toward the robot arm 21.

Figure 15:
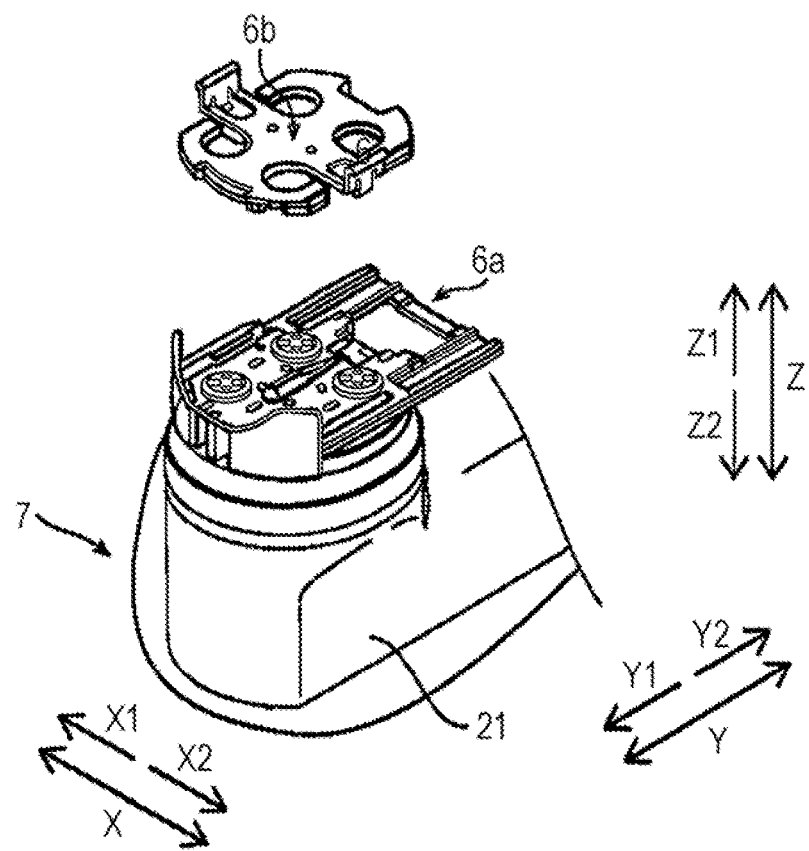
FIG. 15 is a diagram for explaining the removal of the stopper from the adapter attached to the robot arm according to the embodiment.

As illustrated in FIG. 15, when the adapter 6a is attached to the robot arm 21 and each driving transmission member 61 of the adapter 6a fits together with each driving member 21b of the robot arm 21, the stopper 6b is removed from the adapter 6a.

Figure 16:
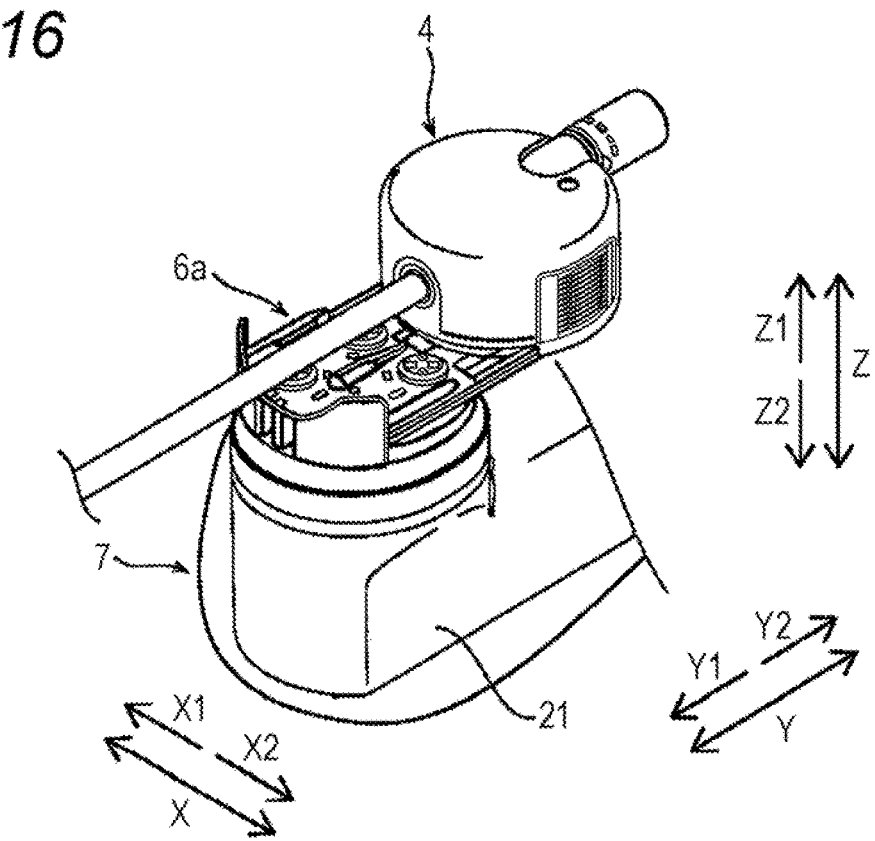
FIG. 16 is a diagram for explaining the attachment of the surgical instrument to the adapter according to the embodiment.

As illustrated in FIG. 16, the surgical instrument 4 is attached to the adapter 6a attached to the robot arm 21. The surgical instrument 4 is attached to the adapter 6a by being slid in the Y direction toward the adapter 6a. With this arrangement, the surgical instrument 4 is attached to the robot arm 21 through the adapter 6a.

Figure 17:
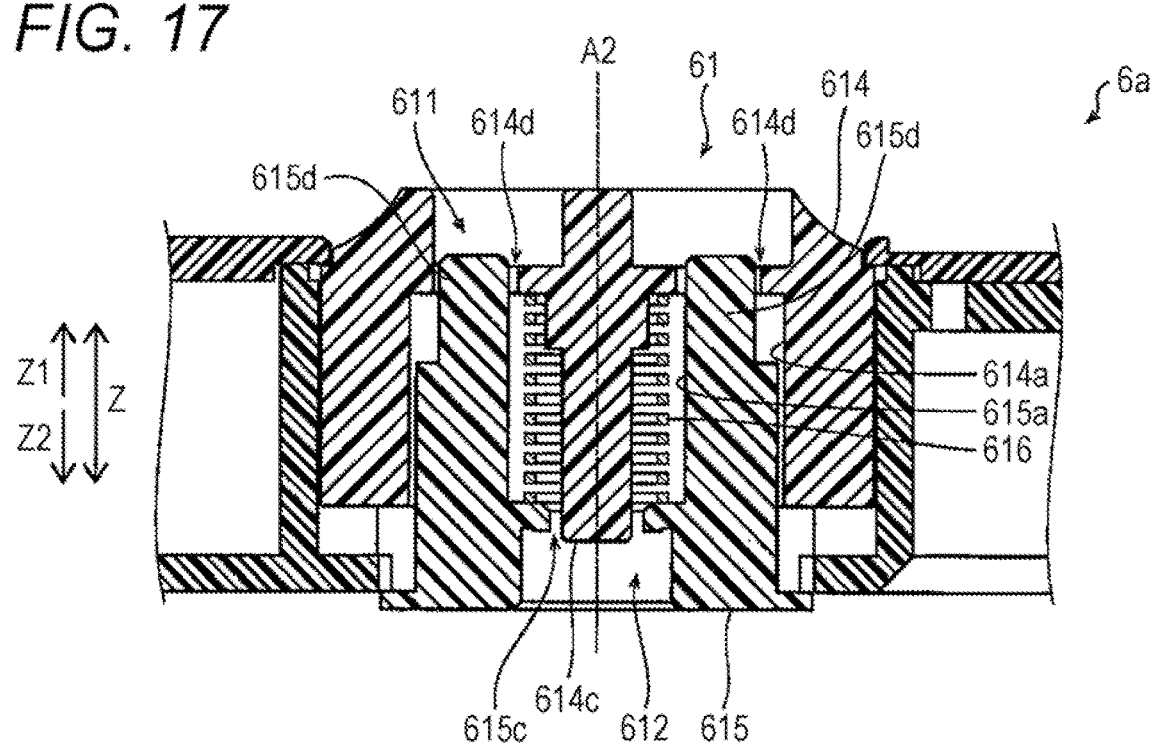
FIG. 17 is a schematic cross-section illustrating the driving transmission member of the adapter according to the embodiment.
Figure 18:
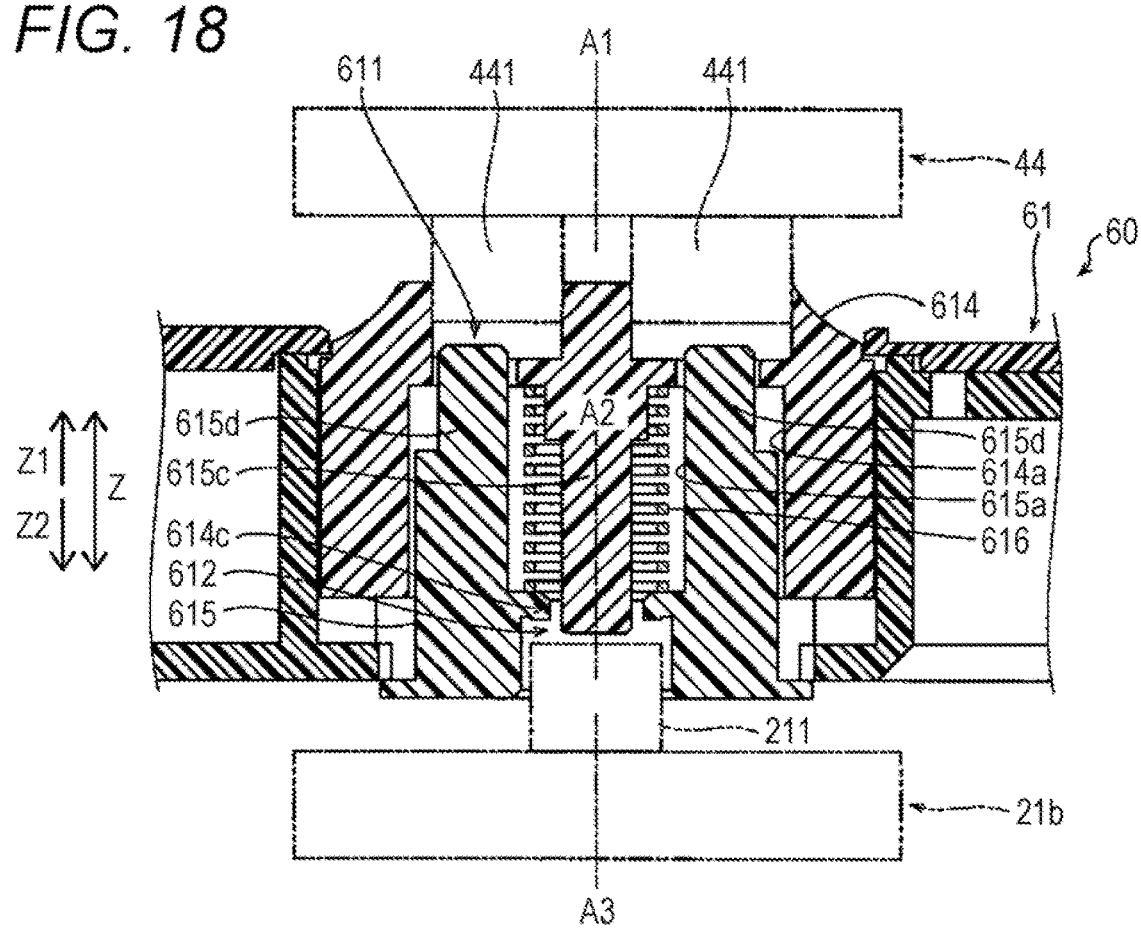
FIG. 18 is a schematic cross-section illustrating a state in which the surgical instrument is mounted and fitted to the adapter according to the embodiment.

Next, FIGS. 17 and 18 will be referenced to describe the state of each driving transmission member 61 in the state in which the adapter 6a is mounted on the driving units 21a of the robot arm 21 and the surgical instrument 4 is mounted on the adapter 6a.

As illustrated in FIG. 18, when each driving member 21b of the robot arm 21 fits together with the corresponding engaging depressed part 612 of the second member 615, the movement of the inserted part 614c of the first member 614 is restricted by the driving member 21b, and the movement of the first member 614 toward the robot arm 21 with respect to the second member 615 is restricted. Additionally, when each driven member 44 of the surgical instrument 4 fits together with the corresponding engaging depressed part 611 of the first member 614, the movement of the projections 615d of the second member 615 is restricted by the driven member 44, and the movement of the second member 615 toward the surgical instrument 4 with respect to the first member 614 is restricted. With this arrangement, a loss of fit between the driving members 21b of the robot arm 21 and the engaging depressed parts 612 of the second member 615 is suppressed.

(Modifications)

Note that the embodiment disclosed herein is for illustrative purposes in all points, and should be considered to be non-limiting. The scope of the present disclosure is indicated by the claims rather than the foregoing description of the embodiment, and all alterations (modifications) performed within the scope of the claims and their equivalents are to be included in the scope of the present disclosure.

The invention claimed is:

1. An adapter set comprising:
   an adapter placed between a driving unit that is provided in a robot arm and includes a driving member, and a surgical instrument that includes a driven member; and
   a stopper mounted on the adapter, wherein
   the adapter includes a rotatably provided driving transmission member configured to transmit a driving force from the driving member of the driving unit to the driven member of the surgical instrument,
   the stopper includes a rotation restricting part configured to restrict a rotation of the driving transmission member,
   the driving transmission member includes a first member that includes a first engaging part configured to fit together with the driven member of the surgical instrument and a second engaging part that is provided separately from the first engaging part and is configured to fit together with the rotation restricting part of the stopper, and a second member that includes a third engaging part configured to fit together with the driving member of the driving unit, and
   the stopper is configured to be mounted on the adapter in a state in which the rotation of the driving transmission member is restricted by the rotation restricting part before the driving member of the driving unit fits together with the second member of the adapter, and is also configured to be removed from the adapter after the driving member of the driving unit fits together with the second member of the adapter.

2. The adapter set according to claim 1, wherein
the first engaging part and the second engaging part are formed as depressed shapes in the first member of the driving transmission member, and
the rotation restricting part of the stopper is formed as a raised shape.

3. The adapter set according to claim 1, wherein the first engaging part and the second engaging part have different shapes as seen in a direction of a rotation axis line of the driving transmission member.

4. The adapter set according to claim 3, wherein the second engaging part is substantially arc-shaped curving along a perimeter of the driving transmission member as seen from the direction of the rotation axis line of the driving transmission member.

5. The adapter set according to claim 3, wherein the first engaging part and the second engaging part have different lengths as seen in a radial direction of the driving transmission member.

6. The adapter set according to claim 1, wherein
the second engaging part is plurally provided with respect to the first engaging part, and
the plurality of second engaging parts are disposed rotationally asymmetrically.

7. The adapter set according to claim 6, wherein the plurality of second engaging parts are disposed line-symmetrically with respect to a straight line passing through a center of rotation of the driving transmission member.

8. The adapter set according to claim 7, wherein the plurality of second engaging parts are disposed in a pair.

9. The adapter set according to claim 1, wherein the second member has a movement restricting part configured to restrict a movement of the second member toward the surgical instrument side by abutting the driven member of the surgical instrument in a case where the driving member of the driving unit is fitted together with the third engaging part of the second member and the driven member of the surgical instrument is fitted together with the first engaging part of the first member.

10. The adapter set according to claim 9, wherein
a through-hole is provided in the first engaging part of the first member,
the movement restricting part includes a projection that extends in the direction of the rotation axis line of the driving transmission member, and
the projection is configured to be inserted into the through-hole of the first engaging part.

11. The adapter set according to claim 1, wherein
the first engaging part of the first member is provided extending in a first direction in a radial direction of the driving transmission member, and
the third engaging part of the second member is provided extending in a second direction substantially orthogonal to the first direction in a radial direction of the driving transmission member.

12. The adapter set according to claim 1, wherein
the second member includes a housing depressed part that houses a spring, and
the first member and the second member fit together to be movable relative to each other with the spring positioned in between.

13. The adapter set according to claim 1, wherein the adapter is configured to be attached to the robot arm through a drape.

14. An adapter placed between a driving unit that is provided in a robot arm and includes a driving member, and a surgical instrument that includes a driven member, the adapter comprising:
a driving transmission member that is rotatably provided and is configured to transmit a driving force from the driving member of the driving unit to the driven member of the surgical instrument, wherein
the driving transmission member includes a first member that includes a first engaging part configured to fit together with the driven member of the surgical instrument and a second engaging part that is provided separately from the first engaging part, and a second member that includes a third engaging part configured to fit together with the driving member of the driving unit, and
before the driving member of the driving unit fits together with the second member, a stopper configured to restrict a rotation of the driving transmission member is mounted to fit together with the second engaging part.

15. The adapter according to claim 14, wherein the first engaging part and the second engaging part have different shapes as seen in a direction of a rotation axis line of the driving transmission member.

16. The adapter according to claim 15, wherein the first engaging part and the second engaging part have different lengths as seen in a radial direction of the driving transmission member.

17. The adapter according to claim 14, wherein
the second engaging part is plurally provided with respect to the first engaging part, and
the plurality of second engaging parts are disposed rotationally asymmetrically.

18. The adapter according to claim 17, wherein the plurality of second engaging parts are disposed line-symmetrically with respect to a straight line passing through a center of rotation of the driving transmission member.

19. The adapter according to claim 14, wherein
the second member has a movement restricting part configured to restrict a movement of the second member toward the surgical instrument side by abutting the driven member of the surgical instrument in a case where the driving member of the driving unit is fitted together with the third engaging part of the second member and the driven member of the surgical instrument is fitted together with the first engaging part of the first member,
a through-hole is provided in the first engaging part of the first member,
the movement restricting part includes a projection that extends in the direction of the rotation axis line of the driving transmission member, and
the projection is configured to be inserted into the through-hole of the first engaging part.

20. A method of mounting a surgical instrument on a robot arm through an adapter that is placed between the robot arm and the surgical instrument and that includes a driving transmission member configured to transmit a driving force from a driving unit of the robot arm to the surgical instrument, the method comprising:
covering the robot arm with a drape;
attaching the adapter to the robot arm covered by the drape, the adapter being in a state in which a stopper configured to restrict a rotation of the driving transmission member is engaged with a second engaging part of the driving transmission member;

causing the driving unit of the robot arm and the driving transmission member of the adapter to engage each other;

removing the stopper from the adapter after the driving unit of the robot arm and the driving transmission member of the adapter have engaged each other; and attaching the surgical instrument to the adapter with the stopper removed, such that the surgical instrument engages with a first engaging part different from the second engaging part of the driving transmission member.

\* \* \* \* \*